United States Patent [19]

Pauling et al.

[11] Patent Number: 5,210,220

[45] Date of Patent: May 11, 1993

[54] METHOD FOR PREPARING DERIVATIVES OF ASCORBIC ACID

[75] Inventors: Horst Pauling, Bottmingen; Christof Wehrli, Witterswil, both of Switzerland

[73] Assignee: Hoffmann-La Roche Inc., Nutley, N.J.

[21] Appl. No.: 773,874

[22] PCT Filed: Mar. 1, 1991

[86] PCT No.: PCT/CH91/00049

§ 371 Date: Oct. 25, 1991

§ 102(e) Date: Oct. 25, 1991

[87] PCT Pub. No.: WO91/13895

PCT Pub. Date: Sep. 19, 1991

[30] Foreign Application Priority Data

Mar. 7, 1990 [CH] Switzerland ............... 731/90

[51] Int. Cl.$^5$ ............... C07D 307/62; C07F 9/06
[52] U.S. Cl. ............... 549/222; 549/315
[58] Field of Search ............... 549/222, 315

[56] References Cited

U.S. PATENT DOCUMENTS

| | | | |
|---|---|---|---|
| 3,658,848 | 4/1972 | Nomura et al. | 549/315 |
| 4,179,445 | 12/1979 | Seib et al. | 549/222 |
| 4,251,449 | 2/1981 | Schreur | 549/222 |
| 4,997,958 | 3/1991 | Pauling et al. | 549/315 |
| 4,999,437 | 3/1991 | Dobler et al. | 549/315 |
| 5,110,950 | 5/1992 | Seib et al. | 549/222 |
| 5,110,951 | 5/1992 | Ishimura et al. | 549/222 |
| 5,118,817 | 6/1992 | Toshida et al. | 549/222 |

FOREIGN PATENT DOCUMENTS

| | | | |
|---|---|---|---|
| 388869 | 9/1990 | European Pat. Off. | 549/315 |
| 1805958 | 5/1969 | Fed. Rep. of Germany | 549/222 |
| 2719303 | 11/1977 | Fed. Rep. of Germany | |
| 1489249 | 7/1967 | France | |
| 1536706 | 8/1968 | France | |
| 4497 | 2/1970 | Japan | 549/222 |
| 15605 | 5/1973 | Japan | 549/222 |
| 7140789 | 8/1982 | Japan | 549/222 |
| 8222078 | 12/1983 | Japan | 549/315 |
| 9051293 | 3/1984 | Japan | 549/222 |
| 9106494 | 6/1984 | Japan | 549/315 |
| 2030791 | 2/1987 | Japan | 549/222 |
| 1158030 | 7/1969 | United Kingdom | |
| 1201404 | 8/1970 | United Kingdom | 549/222 |
| 1334933 | 10/1973 | United Kingdom | 549/315 |
| 2114571 | 8/1983 | United Kingdom | 549/315 |

OTHER PUBLICATIONS

Lee et al., Carbohydrate Research, vol. 67, pp. 127–138 (1978).

Nomura et al., Chem. Pharm. Bull., vol. 19, pp. 1433–1437 (1971).

Computer Search Abstract.

*Primary Examiner*—Cecilia Tsang
*Attorney, Agent, or Firm*—George M. Gould; William H. Epstein

[57] ABSTRACT

The invention is concerned with a process for the manufacture of ascorbyl phosphates, namely of phosphates of the formula

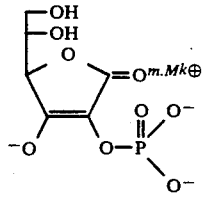

wherein $M^{k\oplus}$ denotes a cation, $k\oplus$ denotes the valency and m denotes the equivalents, with the proviso that the product from k.m=3, by phsophorylating ascorbic acid.

k is 1 to 3, especially 1 or 2.

The process comprises using pre-formed sodium (or potassium) dichlorophosphate as the phosphorylating reagent, adding ascorbic acid to this pre-formed phosphorylating reagent in aqueous solution, especially at pH values between about 11.0 and about 13.0, in the presence of a water-soluble trialkylamine as the catalyst and at temperatures between about +10° C. and about −8° C., especially at temperatures below 0° C., and, if desired, trans-salting the I which is obtained as the sodium (or potassium) salt and/or, if desired, purifying via an amine salt.

10 Claims, No Drawings

METHOD FOR PREPARING DERIVATIVES OF ASCORBIC ACID

The invention is concerned with a process for the manufacture of ascorbyl phosphates, namely of phosphates of the formula

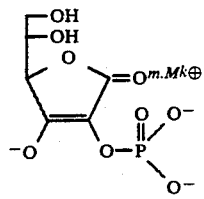

wherein $M^{k\oplus}$ denotes a cation, $k\oplus$ denotes the valency and m denotes the equivalents, with the proviso that the product from $k.m = 3$, by phosphorylating ascorbic acid.

k is 1 to 3, especially 1 or 2.

The process comprises using pre-formed sodium (or potassium) dichlorophosphate as the phosphorylating reagent, adding ascorbic acid to this pre-formed phosphorylating reagent in aqueous solution, especially at pH values between about 11.0 and about 13.0, in the presence of a water-soluble trialkylamine as the catalyst and at temperatures between about $+10°$ C. and about $-8°$ C., especially at temperatures below $0°$ C., and, if desired, trans-salting the I which is obtained as the sodium (or potassium) salt and/or, if desired, purifying via an amine salt.

The preparation of the phosphorylating reagent is preferably carried out in situ, namely from $POCl_3$ and aqueous NaOH or KOH. The ratio of $POCl_3$:base is conveniently about 1:1.5 to about 1:2.5, preferably about 1:2.

The reagent is prepared in a pH range of about 4–11, with the preferred procedure being carried out in a neutral medium.

the phosphorylation is conveniently carried out at temperatures of about $-8°$ C. to about $+10°$ C., with temperatures below $0°$ C. being preferred. This also applies to the separation of the alkali salts described below.

The ascorbic acid is now added to the thus-prepared phosphorylating reagent which is in solution or, if desired, in suspension. This addition is conveniently effected at pH values between about 11 to 13 and at the above temperatures.

The addition of the ascorbic acid to the pre-formed phosphorylating reagent leads to the selectivity which is striven for: the temperature can be held low in a much simpler manner: part of the heat liberated during the hydrolysis is, of course, already dissipated.

A convenient ratio of ascorbic acid:phosphorylating agent is that of about 1:1 to about 1:1.5, with the preferred range lying at about 1:1.35.

The manufacture of the salts I is effected with the addition of a catalyst, namely a water-soluble tert. amine.

The tert. amine is conveniently acyclic, monocylic or bicyclic.

Examples of preferred water-soluble amine are amines having the following groupings:

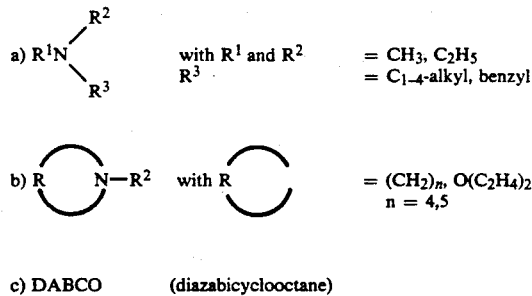

c) DABCO (diazabicyclooctane)

Timethylamine is preferred.

The convenient ratio of ascorbic acid:amine is about 1:0.2 to about 1:1, with the preferred range being 1:0.5.

The addition of the ascorbic acid to the pre-formed phosphorylating reagent is thus effected in a strongly alkaline range.

Spontaneous crystallization of the alkali phosphate takes place, with the Na salt being preferred over the K salt.

After its separation, the trisodium or tripotassium salt I which is present in the filtrate can be trans-salted using a solution of a water-soluble metal salt, whereby the respective most insoluble salt I can be precipitated.

$Ca^{2+}$ and $Mg^{2+}$ are in the foreground of interest here. A chloride is preferably used, but the anion of another mineral acid, for example the nitrate, also comes into consideration.

The preferred concentrations lie in the range of a few mol/liter, e.g. about 1–2 mol/l.

The further purification of the phosphates I (M=Na, K) is preferable carried out with the aid of so-called "crystallization bases" which form salts with acids, in the present instance with the "acidic" form of I.

Especially suitable crystallization bases are bicyclic and tricyclic amino compounds, for example 1- or 2-amino-adamantane, (+)-dehydroabietylamine, etc.

Especially suitable are amino compounds which have the camphane (bornane) or pinane structure, such as e.g.
3-endo-aminoborneaol methyl ether,
[1S]-3-pinanamine,
(−)-cis-myrtanylamine,
with
(+)-3-(aminomethyl)-pinane and
(−)-3-(aminomethyl)-pinane
being especially suitable From this list it will be evident that the lower limit of C atoms in the ring is preferably 9.

Those phosphates I which have as the cation an ammonium ion corresponding to one of the above amino compounds crystallize especially readily, for example from a mixture of lower alcohols, e.g. methanol/water.

As mentioned above, these salts are especially useful for the manufacture of pure ascorbyl phosphates.

The difficulty soluble Ca salt is especially suitable for the vitaminization of fish feed, the readily soluble sodium magnesium salt and the CaH salt, which has a good solubility in water, are especially suitable for the vitaminization of food for mammals.

The salts I find generally applicability for vitaminization in the feed and food sectors where, depending on their solubility, they can be employed in a manner known per se.

EXAMPLE 1

55 ml of 20% NaCl are placed under a protective gas atmosphere. Thereto there are added at −8° C. and at pH 7 (±3) within 20 minutes 12.4 ml of POCl$_3$, 31 ml of 28% NaOH and 100 g of ice. Care must be taken that the pH value of the mixture is always about 7 and that the temperature does not rise above −8° C. There are now added 17.6 g of ascorbic acid (in 33 ml of 3N NaOH), 60 g of ice and 10 ml of 45% trimethylamine. The pH value is held at 12 by the addition of 50 ml of 28% NaOH. The mixture is stirred until the addition of the NaOH has been completed at 5° C. The crystallized-out Na$_3$PO$_4$ is filtered off under suction at −8° C. and pH 13. The filtrate is concentrated to 300 ml in a vacuum and adjusted to pH 10 by the addition of conc. HCl.

This solution containing the trisodium salt of I is added dropwise within one hour to 180 ml of 1 molar CaCl$_2$ solution. The precipitation of the calcium salt has finished after 2 days. The crystallized-out material is filtered off under suction, washed with water and dried in a vacuum. Yield 31 g of calcium L-ascorbic-2-phosphate.3H$_2$O (content 85%).

EXAMPLE 2

300 ml of crude sodium L-ascorbate-2-phosphate solution (pH 10) are combined with 36.6 g of magnesium chloride.6H$_2$O and 440 ml of methanol are added dropwise thereto at room temperature within 4 hours. The precipitation of the magnesium, sodium L-ascorbate-2-phosphate.5H$_2$O has finished after 2days. It is filtered off under suction and washed with 50% aqueous methanol, then with 50 ml of anhydrous methanol. Yield 32 g; content 84%.

EXAMPLE 3

39 g of magnesium, sodium L-ascorbate-2-phosphate pentahydrate (content about 84%) are dissolved in 200 ml of water and treated with a strongly acidic ion exchanger (e.g. DOWEX 50W X8). The acidic solution (free acid of I) is subsequently treated with a solution of 50 g of (−)-3-aminomethylpinane (0.3 mol) in 200 ml of methanol at a pH value of about 7 to 9. The precipitate is dissolved while warming. After seeding the product crystallizes out upon cooling. After suction filtration and drying there are obtained 60.6 g of tris (−)-3-aminomethyl-pinane-L -ascorbate-2-phosphate dihydrate.

To the 60.6 g of tris (−)-3-aminomethylpinane-L-ascorbate-2-phosphate dihydrate are added 229 ml of 1N sodium hydroxide solution and 200 ml of dithyl ether and dissolved while stirring. The aqueous phase is separated and back-washed with diethyl ether. The aqueous phase is concentrated. The product thereby crystallizes out. There are obtained 26.3 g of sodium L-ascorbate-2-phosphate dihydrate=87% of theory with a content of about 99%.

EXAMPLE 4

10 g of calcium L-ascorbate-2-phosphate are dissolved in 55 ml of 1N hydrochloric acid. The solution is concentrated to 30 g in vacuo. 50 ml of methanol are slowly added dropwise thereto within about 3 hours at 0°-10° C. and pH 2-2.4, whereby calcium hydrogen L-ascorbate-2-phosphate crystallizes out. The pH value of the suspension is held at 2-2.4 by the simultaneous addition of 4N sodium hydroxide solution. After standing at 0° C. for 24 hours the product is filtered off under suction, rinsed with 30 ml of methanol and dried at 5020 C. in vacuo for 5 hours. 6.46 g of calcium hydrogen L-ascorbate-2-phosphate are obtained.

We claim:

1. A process for producing an ascorbyl phosphate of the formula:

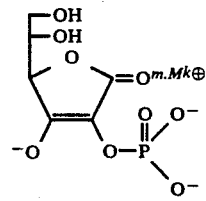

wherein M$^{k\oplus}$ is a cation, k$^\oplus$ is the valency of the cation; and m is the number of equivalents of the cation; with the proviso that the product of K and M is 3, by phosphorylating ascorbic acid comprising mixing ascorbic acid with sodium or potassium dichlorophosphate in an aqueous solution, and phosphorylating said ascorbic acid with said sodium or potassium dichlorophosphate in said aqueous solution in the presence of a water-soluble trialkylamine amine catalyst and at a temperature of at most 10° C. to produce said ascorbyl phosphate.

2. The process of claim 1, wherein said phosphorylation is carried out in said solution at a pH of from about 11.0 to about 13.0.

3. The process of claim 2, wherein said temperature is from +10° C. to about −8° C.

4. The process of claim 1, wherein the dichlorophosphate is formed in situ in the aqueous solution prior to being mixed with ascorbic acid.

5. A process according to claim 1, wherein an acyclic, mono- or bicyclic tert. amine is used as the catalyst.

6. An ascorbyl phosphate of the formula:

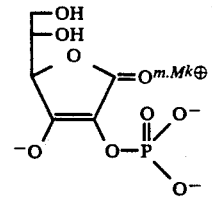

wherein M$^{k\oplus}$ is a cation k$^\oplus$ is the valency of the cation; and m is the number of equivalents of the cation; with the proviso the product of K and M is 3.

7. The ascorbyl phosphorylate of claim 6 wherein M$^{k\oplus}$ is NH$_4$+ and m is 3.

8. NaMg L-ascorbate-2-phosphate.

9. CaH L-ascorbate-2-phosphate.

10. Tris-(−)-3-aminomethylpinane-L-ascorbate-2-phosphate.

* * * * *